US010588593B2

(12) United States Patent
Yamazaki

(10) Patent No.: US 10,588,593 B2
(45) Date of Patent: Mar. 17, 2020

(54) X-RAY CT APPARATUS AND X-RAY DETECTOR

(71) Applicant: Toshiba Medical Systems Corporation, Otawara-shi (JP)

(72) Inventor: Masahiko Yamazaki, Utsunomiya (JP)

(73) Assignee: Canon Medical Systems Corporation, Otawara-shi (JP)

(*) Notice: Subject to any disclaimer, the term of this patent is extended or adjusted under 35 U.S.C. 154(b) by 975 days.

(21) Appl. No.: 14/941,952

(22) Filed: Nov. 16, 2015

(65) Prior Publication Data

US 2016/0066876 A1 Mar. 10, 2016

Related U.S. Application Data

(63) Continuation of application No. PCT/JP2014/061515, filed on Apr. 24, 2014.

(30) Foreign Application Priority Data

May 28, 2013 (JP) .................................. 2013-112143

(51) Int. Cl.
*A61B 6/00* (2006.01)
*A61B 6/03* (2006.01)
*G01T 1/29* (2006.01)

(52) U.S. Cl.
CPC ............... *A61B 6/56* (2013.01); *A61B 6/03* (2013.01); *A61B 6/032* (2013.01); *A61B 6/42* (2013.01);
(Continued)

(58) Field of Classification Search
CPC ........... A61B 6/032; A61B 6/035; A61B 6/42; A61B 6/4233; A61B 6/4241;
(Continued)

(56) References Cited

U.S. PATENT DOCUMENTS 5,530,424 A * 6/1996 Harrison ................ A61B 6/56
340/500
5,912,942 A * 6/1999 Schick ................ G01T 1/2018
250/370.09

(Continued)

FOREIGN PATENT DOCUMENTS

JP 2010-075454 A 4/2010
JP 2011-226902 A 11/2011
JP 2012-187144 A 10/2012

OTHER PUBLICATIONS

International Search Report dated Jun. 10, 2014 for PCT/JP2014/061515 filed Apr. 24, 2014 with English Translation.

*Primary Examiner* — Allen C. Ho
(74) *Attorney, Agent, or Firm* — Oblon, McClelland, Maier & Neustadt, L.L.P.

(57) ABSTRACT

According to one embodiment, an X-ray CT apparatus includes a fixed part, a rotating part, a detector, an A/D converter, a data transmitter, and a wireless transceiver. The rotating part is configured to be rotatably attached to the fixed part to rotate around a subject. The detector is arranged in the rotating part, and detects X-rays emitted from an irradiator and generates an analog signal. The A/D converter is arranged in the rotating part, and converts the analog signal to a digital signal. The data transmitter is arranged in the rotating part, and, upon receipt of the digital signal from the A/D converter, transmits the digital signal to a data receiver arranged in the fixed part. The wireless transceiver wirelessly transmits and receives signals in at least a part between the detector and the A/D converter or between the A/D converter and the data transmitter.

8 Claims, 7 Drawing Sheets

(52) U.S. Cl.
CPC .......... *A61B 6/4208* (2013.01); *A61B 6/4233* (2013.01); *A61B 6/4241* (2013.01); *A61B 6/4266* (2013.01); *A61B 6/44* (2013.01); *A61B 6/4411* (2013.01); *A61B 6/4429* (2013.01); *A61B 6/4435* (2013.01); *A61B 6/4441* (2013.01); *A61B 6/4447* (2013.01); *A61B 6/563* (2013.01); *A61B 6/566* (2013.01); *G01T 1/2985* (2013.01); *A61B 6/035* (2013.01)

(58) Field of Classification Search
CPC ......... A61B 6/4266; A61B 6/56; A61B 6/563; A61B 6/44; A61B 6/4429; A61B 6/4435; A61B 6/4441; A61B 6/4447; A61B 6/566; A61B 6/4208; A61B 6/4411
USPC ............. 378/19, 62, 91, 98.8, 196–198, 15; 250/370.09
See application file for complete search history.

(56) References Cited

U.S. PATENT DOCUMENTS

| | | | | |
|---|---|---|---|---|
| 5,991,358 | A * | 11/1999 | Dolazza | A61B 6/032 378/19 |
| 6,081,576 | A * | 6/2000 | Schanen | A61B 6/032 378/19 |
| 6,198,791 | B1 * | 3/2001 | He | A61B 6/032 378/12 |
| 6,292,528 | B1 * | 9/2001 | Wieczorek | A61B 6/032 250/363.02 |
| 6,292,919 | B1 * | 9/2001 | Fries | A61B 6/56 714/746 |
| 6,972,411 | B2 * | 12/2005 | Schick | A61B 6/145 250/370.11 |
| 7,015,478 | B2 * | 3/2006 | Yamamoto | A61B 6/00 250/370.08 |
| 7,072,443 | B2 * | 7/2006 | Schick | A61B 5/0088 378/98.8 |
| 7,421,063 | B2 * | 9/2008 | Takenaka | G01T 1/244 378/116 |
| 7,545,914 | B2 * | 6/2009 | Kito | A61B 6/4283 378/207 |
| 7,561,668 | B2 * | 7/2009 | Ohta | G03B 42/04 378/102 |
| 7,593,507 | B2 * | 9/2009 | Ohta | A61B 6/032 378/207 |
| 7,638,773 | B2 * | 12/2009 | Kuwabara | G03B 42/04 250/370.08 |
| 7,655,916 | B2 * | 2/2010 | Ohta | G01T 7/00 250/370.08 |
| 7,712,959 | B2 * | 5/2010 | Tanabe | H01J 31/49 250/370.08 |
| 7,732,779 | B2 * | 6/2010 | Kito | G01T 7/00 250/370.09 |
| 7,737,427 | B2 * | 6/2010 | Kito | A61B 6/4233 250/370.08 |
| 7,740,405 | B2 * | 6/2010 | Ohta | H01J 31/49 378/189 |
| 7,767,981 | B2 * | 8/2010 | Kuwabara | A61B 6/4216 250/484.4 |
| 7,772,560 | B2 * | 8/2010 | Ohta | A61B 6/00 250/370.09 |
| 7,777,192 | B2 * | 8/2010 | Ohta | A61B 6/00 250/370.09 |
| 7,777,193 | B2 * | 8/2010 | Kito | G01T 7/00 250/370.09 |
| 7,787,594 | B2 * | 8/2010 | Ohta | A61B 6/4233 378/114 |
| 7,807,976 | B2 * | 10/2010 | Ohta | A61B 6/4233 250/370.09 |
| 7,829,859 | B2 * | 11/2010 | Yoshimi | G03B 42/04 250/370.08 |
| 7,834,322 | B2 * | 11/2010 | Yoshimi | A61B 6/4283 250/370.09 |
| 7,847,277 | B2 * | 12/2010 | Kito | A61B 6/00 250/580 |
| 7,888,649 | B2 * | 2/2011 | Kito | A61B 6/4283 250/370.09 |
| 7,894,575 | B2 * | 2/2011 | Tsubota | A61B 6/548 378/96 |
| 7,918,603 | B2 * | 4/2011 | Ohta | A61B 6/04 378/189 |
| 7,935,931 | B2 * | 5/2011 | Ohta | G01T 7/00 250/370.08 |
| 7,991,119 | B2 * | 8/2011 | Yoshida | G01T 1/00 378/114 |
| 7,999,234 | B2 * | 8/2011 | Ohta | A61B 6/4283 250/336.1 |
| 8,050,383 | B2 * | 11/2011 | Ohta | A61B 6/00 378/62 |
| 8,053,727 | B2 * | 11/2011 | Nishino | G03B 42/04 250/336.1 |
| 8,080,802 | B2 * | 12/2011 | Nishino | A61B 6/4233 250/370.08 |
| 8,112,000 | B2 * | 2/2012 | Nishino | H04B 10/1143 398/140 |
| 8,182,147 | B2 * | 5/2012 | Nishino | A61B 6/00 378/189 |
| 8,203,446 | B2 * | 6/2012 | Tsubota | H04W 48/02 340/539.1 |
| 8,229,202 | B2 * | 7/2012 | Kito | A61B 6/00 378/114 |
| 8,259,904 | B2 * | 9/2012 | Tsubota | A61B 6/00 378/116 |
| 8,265,225 | B2 * | 9/2012 | Nishino | A61B 6/4283 378/102 |
| 8,270,564 | B2 * | 9/2012 | Chiang | A61B 6/032 378/116 |
| 8,330,597 | B2 * | 12/2012 | Nishino | A61B 6/4283 250/370.01 |
| 8,334,515 | B2 * | 12/2012 | Tsubota | A61B 6/548 250/370.08 |
| 8,334,516 | B2 * | 12/2012 | Tsubota | A61B 6/4283 250/370.08 |
| 8,357,908 | B2 * | 1/2013 | Kuwabara | A61B 6/548 250/370.08 |
| 8,378,309 | B2 * | 2/2013 | Enomoto | H04N 5/32 250/370.08 |
| 8,421,024 | B2 * | 4/2013 | Ohta | G03B 42/02 250/370.08 |
| 8,451,974 | B2 * | 5/2013 | Morton | G21K 1/025 378/57 |
| 8,532,262 | B2 * | 9/2013 | Iwakiri | A61B 6/4233 250/370.09 |
| 8,546,777 | B2 * | 10/2013 | Utsunomiya | A61B 6/4283 250/580 |
| 8,552,392 | B2 * | 10/2013 | Kito | G03B 42/04 250/370.09 |
| 8,654,926 | B2 * | 2/2014 | Ohta | G01T 1/243 378/114 |
| 8,675,624 | B2 * | 3/2014 | Tachikawa | A61B 6/4494 370/338 |
| 8,837,669 | B2 * | 9/2014 | Morton | A61B 6/022 378/41 |
| 8,861,678 | B2 * | 10/2014 | Liu | H05G 1/08 378/91 |
| 8,885,795 | B2 * | 11/2014 | Enomoto | H04N 5/32 250/370.09 |
| 8,891,733 | B2 * | 11/2014 | Liu | A61B 6/42 378/91 |
| 9,111,379 | B2 * | 8/2015 | Gregerson | G06T 11/003 |
| 9,125,613 | B2 * | 9/2015 | Gregerson | A61B 6/4488 |
| 9,138,195 | B2 * | 9/2015 | Krupica | G01N 23/046 |
| 9,380,988 | B2 * | 7/2016 | Kitano | A61B 6/4283 |
| 9,492,137 | B2 * | 11/2016 | Iwamoto | A61B 6/4283 |
| 9,532,759 | B2 * | 1/2017 | Taguchi | A61B 6/032 |
| 9,536,302 | B2 * | 1/2017 | Nakano | A61B 6/504 |
| 9,538,107 | B2 * | 1/2017 | Chappo | A61B 6/032 |
| 9,538,978 | B2 * | 1/2017 | Makino | G16H 40/63 |
| 9,585,625 | B2 * | 3/2017 | Sakai | A61B 6/032 |

(56) References Cited

U.S. PATENT DOCUMENTS

| | | | |
|---|---|---|---|
| 9,595,101 B2* | 3/2017 | Kato | G06T 11/005 |
| 9,655,567 B2* | 5/2017 | Takanaka | A61B 6/032 |
| 9,681,850 B2* | 6/2017 | Park | A61B 6/542 |
| 9,689,996 B2* | 6/2017 | Rao | H01L 27/14661 |
| 9,808,159 B2* | 11/2017 | Shizukuishi | H01L 27/14661 |
| 9,810,793 B2* | 11/2017 | Yamazaki | G01N 23/046 |
| 9,818,182 B2* | 11/2017 | Ueki | A61B 6/504 |
| 9,968,323 B2* | 5/2018 | Yamazaki | A61B 6/032 |
| 10,022,100 B2* | 7/2018 | Iijima | A61B 6/4441 |
| 10,217,246 B2* | 2/2019 | Takayama | G01N 23/046 |
| 10,258,296 B2* | 4/2019 | Hiraoka | A61B 6/032 |
| 10,357,214 B2* | 7/2019 | Kimura | A61B 6/03 |
| 2010/0080360 A1 | 4/2010 | Ohta et al. | |

* cited by examiner

US 10,588,593 B2

X-RAY CT APPARATUS AND X-RAY DETECTOR

CROSS-REFERENCE TO RELATED APPLICATION

This application is based upon and claims the benefit of priority from Japanese Patent Application No. 2013-112143, filed May 28, 2013; the entire contents of which are incorporated herein by reference.

FIELD

Embodiments described herein relate generally to an X-ray CT apparatus and an X-ray detector.

BACKGROUND

Among X-ray detectors used in X-ray computed tomography (CT) apparatuses are those provided with a data acquisition system (DAS). For example, a general X-ray detector with DAS amplifies analog signals based on detected X-rays in units of detector elements. After that, the X-ray detector converts the analog signals into digital signals, and controls the transmission of the digital signals in units of modules consisting of a number of detector elements. On this occasion, inside the X-ray detector, data is transferred via wire using a flexible printed circuit (FPC), a connector, and the like.

DETAILED DESCRIPTION

Figure 1:
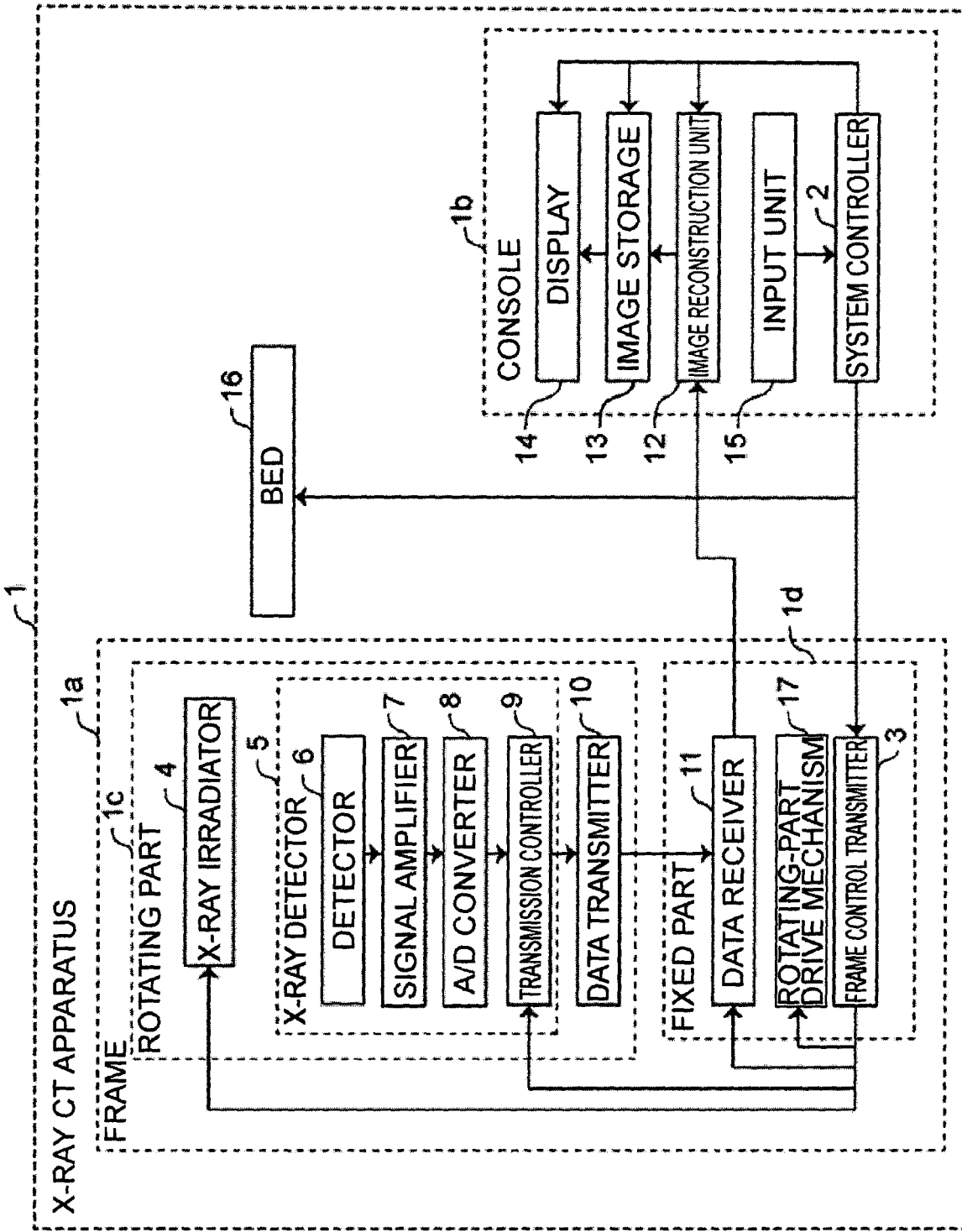
FIG. 1 is a block diagram illustrating the configuration of an X-ray CT apparatus according to an embodiment.

In general, according to one embodiment, an X-ray CT apparatus includes a fixed part, a rotating part, a detector, an analog-to-digital (A/D) converter, a data transmitter, and a wireless transceiver. The rotating part is configured to be rotatably attached to the fixed part to rotate around a subject. The detector is arranged in the rotating part, and detects X-rays emitted from an irradiator and generates an analog signal. The A/D converter is arranged in the rotating part, and converts the analog signal to a digital signal. The data transmitter is arranged in the rotating part, and, upon receipt of the digital signal from the A/D converter, transmits the digital signal to a data receiver arranged in the fixed part. The wireless transceiver wirelessly transmits and receives signals in at least a part between the detector and the A/D converter or between the A/D converter and the data transmitter.

Referring now to the drawings, illustrative embodiments are described below.

FIG. 1 is a block diagram of an X-ray CT apparatus 1 according to an embodiment.

As illustrated in FIG. 1, the X-ray CT apparatus 1 of the embodiment includes a frame 1a, a console 1b, and a bed 16. The frame 1a includes a rotating part 1c and a fixed part 1d. The fixed part 1d is connected to, for example, an external power source (not illustrated), and supplies power and signals to parts constituting the rotating part 1c via a power/signal supply unit such as a slip ring. The rotating part 1c includes an X-ray irradiator 4, an X-ray detector 5, and a data transmitter 10, and is rotatably attached to the fixed part 1d. The fixed part 1d includes a frame control transmitter 3, a data receiver 11, and a rotating-part drive mechanism 17. The console 1b includes a system controller 2, an image reconstruction unit 12, an image storage 13, a display 14, and an input unit 15.

Figure 2:
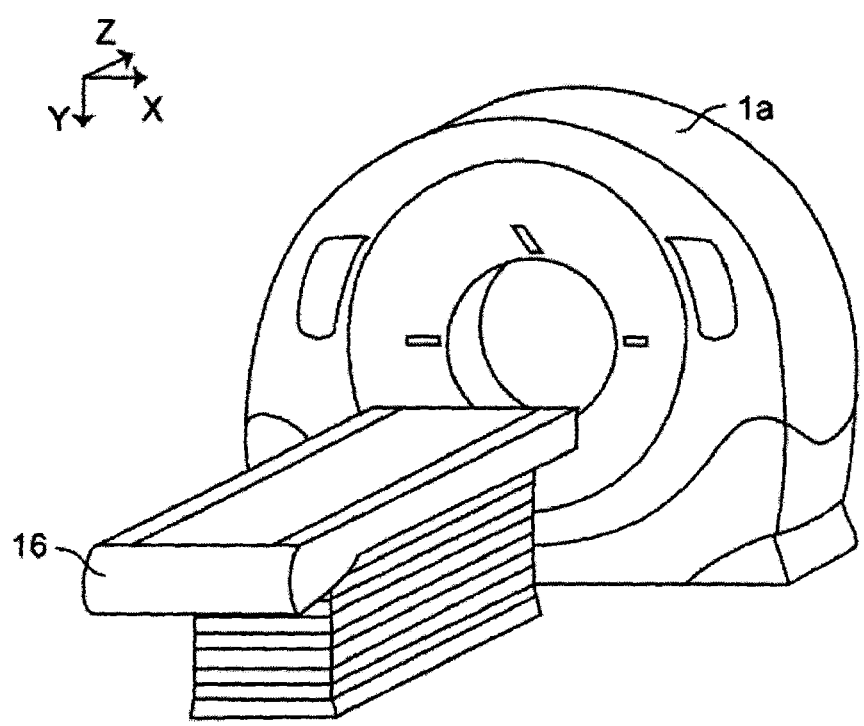
FIG. 2 is a perspective view of the X-ray CT apparatus of the embodiment.

FIG. 2 is a perspective view of the X-ray CT apparatus 1 of the embodiment. In the following description, as illustrated in FIG. 2, Z-axis is an axis extending along the body axis of a patient (subject) placed on the bed 16, Y-axis is an axis extending in the vertical directions, and X-axis is an axis extending perpendicular to the Z-axis and the Y-axis.

The system controller 2 notifies the frame control transmitter 3 of a control content for the X-ray irradiator 4, a transmission controller 9, the data receiver 11, and the rotating-part drive mechanism 17. The system controller 2 displays a predetermined input screen on the display 14 at a predetermined timing. According to an instruction from the operator provided through the input unit 15 or at a predetermined timing, the system controller 2 displays an image on the display 14 based on image data stored in the image storage 13. The system controller 2 notifies the image reconstruction unit 12 of a control content for the transmission controller 9. The system controller 2 moves the bed 16 according to an instruction from the operator provided through the input unit 15 to move the position of a patient placed thereon.

The frame control transmitter 3 transmits the notification from the system controller 2 to the X-ray irradiator 4, the transmission controller 9, the data receiver 11, and the rotating-part drive mechanism 17.

According to the control content received from the frame control transmitter 3, the X-ray irradiator 4 irradiates X-rays at a predetermined intensity in a predetermined range. The X-ray irradiator 4 stops the irradiation of X-rays according to the control content received from the frame control transmitter 3.

The X-ray detector 5 includes a detector 6, a signal amplifier 7, an A/D converter 8, and the transmission controller 9. The X-ray detector 5 is irradiated with X-rays by the X-ray irradiator 4, and detects X-rays having passed through the patient placed on the bed 16 with the detector 6. The detector 6 generates analog signals based on the intensity of the X-rays detected and transmits the analog signals to the signal amplifier 7. The signal amplifier 7 amplifies the analog signals received from the detector 6, and transmits them to the A/D converter 8. The A/D converter 8 converts the analog signals having been amplified and received from the signal amplifier 7 to digital signals, and transmits the digital signals to the transmission controller 9. The transmission controller 9 transmits the digital signals received from the A/D converter 8 to the data transmitter 10 according to the control content received from the frame control transmitter 3. The configuration of the X-ray detector 5 is described in detail later.

The data transmitter 10 transmits the digital signals received from the transmission controller 9 to the data receiver 11 using a communication means such as, for example, optical communication.

According to an instruction from the frame control transmitter 3, the data receiver 11 transmits the digital signals received from the data transmitter 10 to the image reconstruction unit 12 in the console 1b.

According to an instruction from the system controller 2, the image reconstruction unit 12 generates image data based on the digital signals received from the data receiver 11, and transmits the image data to the image storage 13.

The image storage 13 stores the image data received from the image reconstruction unit 12.

According to an instruction from the system controller 2, the display 14 displays an image based on the image data stored in the image storage 13. Besides, according to an instruction from the system controller 2, the display 14 displays a predetermined input screen.

The input unit 15 includes, for example, a mouse, a track ball, and a keyboard, and issues an instruction to the system controller 2 according to an input provided by the operator.

The bed 16 operates according to an instruction from the system controller 2 to move the position of the patient placed thereon in the directions of the X axis, the Y axis, and the Z axis.

The rotating-part drive mechanism 17 operates according to an instruction from the frame control transmitter 3, and rotates the rotating part 1c. In addition, according to an instruction from the frame control transmitter 3, the rotating-part drive mechanism 17 stops the rotation of the rotating part 1c.

The configuration of the X-ray detector 5 is described in detail below.

Figure 3:
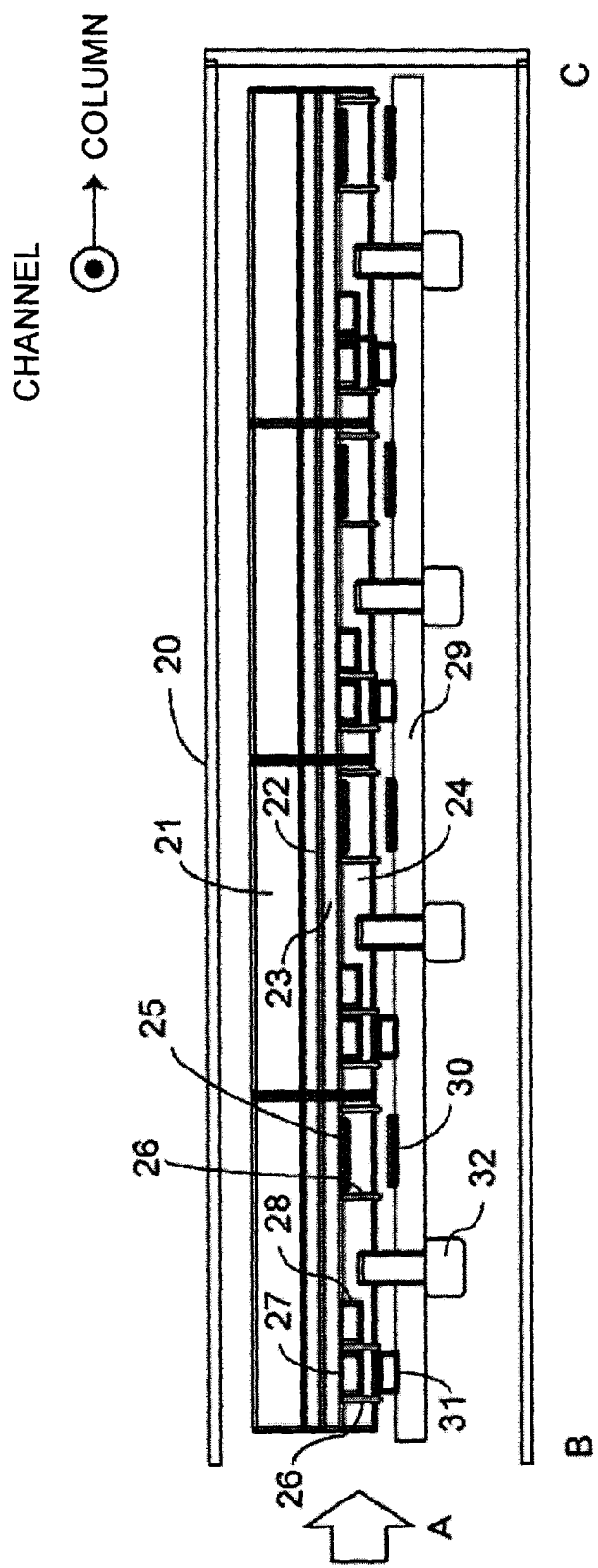
FIG. 3 is a schematic diagram illustrating the internal structure of an X-ray detector of the embodiment.
Figure 4:
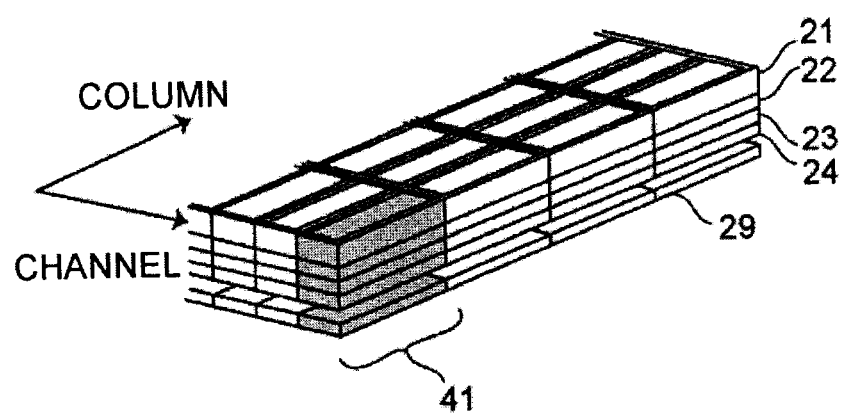
FIG. 4 is another schematic diagram illustrating the internal structure of the X-ray detector of the embodiment.

FIGS. 3 and 4 are schematic views illustrating the internal structure of the X-ray detector 5 of the embodiment. FIG. 3 schematically illustrates an example of a cross-sectional view taken along a section line extending in the column direction. In FIG. 3, the horizontal direction indicates the column direction that corresponds to the Z-axis direction in FIG. 2, while the vertical direction indicates the Y-axis direction in FIG. 2. The direction perpendicular to the paper surface indicates a channel direction that corresponds to the direction of the curvature of the detection surface of X-ray detector 5. Incidentally, the column direction may be opposite to that indicated in FIG. 3.

As illustrated in FIG. 3 or 4, the X-ray detector 5 includes scintillators 21, photodiode chips 22, DAS chips 23, substrates 24, data-transfer radio-wave transmitters 25, shields 26, power-supply radio-wave receivers 27, storage batteries 28, a backplane 29, data-transfer radio-wave receivers 30, power-supply radio-wave transmitters 31, and positioning pins 32. The X-ray detector 5 is inserted in a housing 20 in, for example, the direction indicated by arrow A (Z-axis direction) at the time of the manufacture or maintenance to be installed therein. The scintillators 21 and the photodiode chips 22 correspond to, for example, the detector 6 in FIG. 1. The DAS chips 23 correspond to, for example, the signal amplifier 7, the A/D converter 8, and the transmission controller 9 in FIG. 1.

As illustrated in FIG. 3, each of the substrates 24 supports the data-transfer radio-wave transmitter 25, the shield 26, the power-supply radio-wave receiver 27 and the storage battery 28, and is configured to be removably attached to the X-ray CT apparatus 1 (the X-ray detector 5, the backplane 29). The backplane 29 (support member) supports the data-transfer radio-wave receivers 30 (receiver), the power-supply radio-wave transmitters 31, and the positioning pins 32. The positioning pin 32 is configured to be inserted in a recess formed in the substrate 24. While the positioning pin 32 is inserted in the recess in the substrate 24, the position of the backplane 29 is secured to the substrate 24. When the positioning pin 32 is located in the recess, the data-transfer radio-wave transmitter 25 faces the data-transfer radio-wave receiver 30, and the power-supply radio-wave receiver 27 faces the power-supply radio-wave transmitter 31. The distance between the data-transfer radio-wave transmitter 25 and the data-transfer radio-wave receiver 30, and the distance between the power-supply radio-wave receiver 27 and the power-supply radio-wave transmitter 31 are determined by, for example, the length of the positioning pin 32 or the depth of the recess. Note that although FIG. 3 illustrates an example in which the positioning pin 32 is arranged on the backplane 29 and the recess is formed in the substrate 24, the positioning pin 32 may be arranged on the substrate 24 and the recess may be formed in the backplane 29.

The X-ray detector 5 is provided with the scintillator 21, the photodiode chip 22, the DAS chip 23, the substrate 24, the data-transfer radio-wave transmitter 25, the shield 26, the power-supply radio-wave receiver 27, the storage battery 28, the data-transfer radio-wave receiver 30, the power-supply radio-wave transmitter 31, and the positioning pin 32, for example, in units of modules 41, which are divided in at least the body axis direction of the subject as illustrated in FIG. 4. In this embodiment, the X-ray detector 5 includes, for example, four arrays of 38 (4×38) modules, in which arrays of four modules are arranged in the column direction, and arrays of 38 modules are arranged in the channel direction. Note that the column direction corresponds to the Z-axis direction in FIG. 2, and the channel direction corresponds to the curvature direction of the detection surface of the X-ray detector 5.

After passing through the patient placed on the bed 16, X-rays emitted from the X-ray irradiator 4 are collimated by a collimator (not illustrated), and then incident on the scintillator 21.

The scintillator 21 converts the incident X-rays into light. The light generated in the scintillator 21 is incident on the photodiode chip 22.

The photodiode chip 22 includes, for example, (64×24) photodiode elements (detector elements), in which arrays of 64 photodiode elements are arranged in the column direction, and arrays of 24 photodiode elements are arranged in the channel direction. The photodiode chip 22 generates analog signals based on the incident light in units of photodiode elements. The photodiode chip 22 transmits the analog signals to the DAS chip 23 by differentiating them in units of photodiode elements.

The DAS chip 23 amplifies the analog signals received from the photodiode chip 22 in units of photodiode elements. The DAS chip 23 then converts the analog signals thus amplified into digital signals in units of photodiode elements. According to the control content received from the frame control transmitter 3, the DAS chip 23 transmits the digital signals to the data-transfer radio-wave transmitter 25.

The data-transfer radio-wave transmitter 25 is a wireless communication unit (wireless transceiver, wireless communication part, wireless communication circuit), and converts the digital signals received from the DAS chip 23 into radio waves of a predetermined frequency using electrical energy stored in the storage battery 28. The data-transfer radio-wave transmitter 25 transmits the radio waves to the data-transfer radio-wave receiver 30 in serial, for example, in units of arrays of photodiode elements of the modules 41.

The shield 26 has, for example, radio-wave shielding function. The shield 26 guides the radio waves transmitted from the data-transfer radio-wave transmitter 25 to the corresponding data-transfer radio-wave receiver 30 such that the radio waves are exchanged only between the data-transfer radio-wave transmitter 25 and the data-transfer radio-wave receiver 30 in a corresponding relationship so as not to affect the other modules 41. The corresponding relationship as used herein indicates the constituent elements of the same module 41. In addition, the shield 26 guides the radio wave transmitted from the power-supply radio-wave transmitter 31 to the corresponding power-supply radio-wave receiver 27 such that the radio wave is exchanged only between the power-supply radio-wave transmitter 31 and the power-supply radio-wave receiver 27 in a corresponding relationship so as not to affect the other modules 41.

The data-transfer radio-wave receiver 30 is a wireless communication unit (wireless transceiver, wireless communication part, wireless communication circuit), and generates digital signals based on the radio waves transmitted from the data-transfer radio-wave transmitter 25 and guided by the shield 26. The data-transfer radio-wave receiver 30 transmits the digital signals to the data transmitter 10.

The power-supply radio-wave transmitter 31 is a wireless power supply unit (radio power supply), and converts a current supplied from the fixed part 1*d* into a radio wave. The power-supply radio-wave transmitter 31 transmits the radio wave to the power-supply radio-wave receiver 27.

The power-supply radio-wave receiver 27 is a wireless power supply unit (radio power supply), and converts the radio wave transmitted from the power-supply radio-wave transmitter 31 and guided by the shield 26 into a current. The power-supply radio-wave receiver 27 sends the current to the storage battery 28.

The storage battery 28 is charged by the current fed from the power-supply radio-wave receiver 27, and stores electrical energy. When the data-transfer radio-wave transmitter 25 converts the digital signal into a radio wave, the storage battery 28 supplies the electrical energy stored therein to the data-transfer radio-wave transmitter 25.

Figure 5:
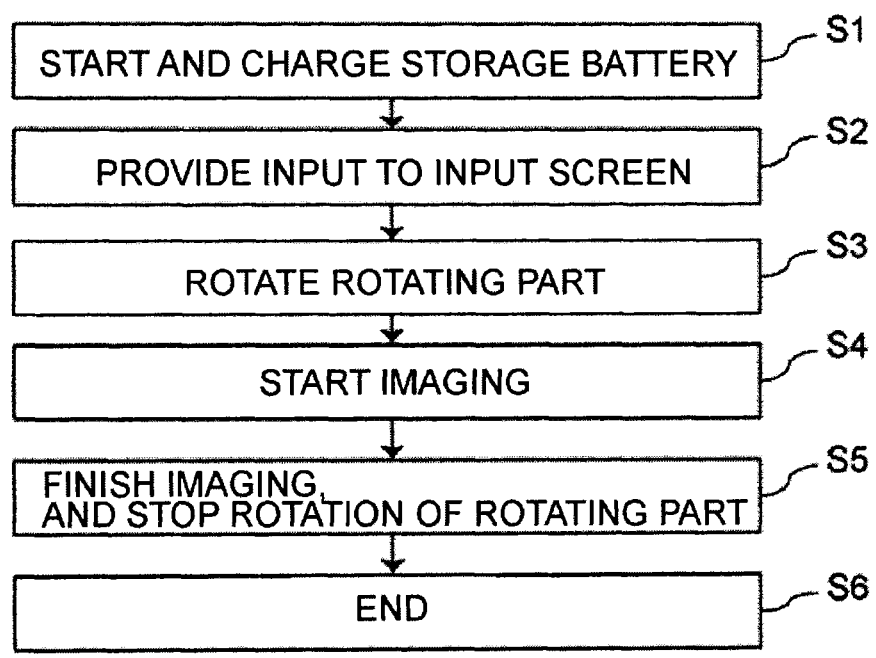
FIG. 5 is a flowchart of the operation of the X-ray CT apparatus of the embodiment.

FIG. 5 is a flowchart of the operation of the X-ray CT apparatus 1 of the embodiment. The process related to the X-ray detector 5 is described in connection with FIGS. 3 and 4.

In step S1, the X-ray CT apparatus 1 starts the operation. When the operation of the X-ray CT apparatus 1 is started, the fixed part 1*d* supplies a current to the power-supply radio-wave transmitter 31 of the X-ray detector 5 in the rotating part 1*c* based on electric power supplied from an external power supply. The power-supply radio-wave transmitter 31 converts the current into a radio wave, and transmits the radio wave to the power-supply radio-wave receiver 27. The storage battery 28 is charged by the current fed from the power-supply radio-wave receiver 27, and stores electrical energy. Besides, when the X-ray CT apparatus 1 is activated, the process proceeds to step S2.

In step S2, the system controller 2 displays a predetermined input screen on the display 14. According to an instruction from the system controller 2, the display 14 displays a predetermined input screen thereon. The predetermined input screen is used to set, for example, the intensity of X-rays, the irradiation range of X-rays, the irradiation time of X-rays, the rotational speed of the rotating part 1*c*, and the like, each of which is related to imaging. The operator provides an input to the input screen using the input unit 15. Upon completion of providing the input to the predetermined input screen, the operator places the patient on the bed 16, and enters an instruction by using the input unit 15 to move the position of the patient to the imaging position. According to the instruction from the operator provided through the input unit 15, the system controller 2 moves the position of the patient to the imaging position. When the position of the patient is moved to the imaging position in response to the input provided by the operator, the process proceeds to step S3.

In step S3, the operator provides an instruction to the system controller 2 by using the input unit 15 to rotate the rotating part 1*c*. According to the instruction from the operator provided through the input unit 15, the system controller 2 notifies the frame control transmitter 3 of a control content for the rotating-part drive mechanism 17. The frame control transmitter 3 transmits the control content notified by the system controller 2 to the rotating-part drive mechanism 17. According to the control content received from the frame control transmitter 3, the rotating-part drive mechanism 17 rotates the rotating part 1*c* up to a speed based on the settings entered in step S2. When the rotating part 1*c* comes to rotate at the speed, the process proceeds to step S4.

In step S4, the system controller 2 notifies the frame control transmitter 3 of a control content for the X-ray irradiator 4 based on the settings entered in step S2. The frame control transmitter 3 transmits the notification from the system controller 2 to the X-ray irradiator 4. The X-ray irradiator 4 sets the irradiation range of X-rays based on the control content received from the frame control transmitter 3, and irradiates X-rays at an intensity based on the control content received from the frame control transmitter 3. After passing through the patient placed on the bed 16, X-rays emitted from the X-ray irradiator 4 are collimated by a collimator (not illustrated), and then incident on the scintillator 21. The scintillator 21 converts the incident X-rays into light. The light generated in the scintillator 21 is incident on the photodiode chip 22. The photodiode chip 22 generates analog signals based on the incident light in units of photodiode elements. The photodiode chip 22 transmits the analog signals to the DAS chip 23 by differentiating them. The DAS chip 23 amplifies the analog signals received from the photodiode chip 22 in units of photodiode elements. The DAS chip 23 then converts the analog signals into digital signals in units of photodiode elements. According to the control content received from the frame control transmitter 3, the DAS chip 23 transmits the digital signals to the data-transfer radio-wave transmitter 25. The data-transfer radio-wave transmitter 25 converts the digital signals received from the DAS chip 23 into radio waves of a predetermined frequency using the electrical energy accumulated in the storage battery 28 from step S1. The data-transfer radio-wave transmitter 25 transmits the radio waves to the data-transfer radio-wave receiver 30. The shield 26 guides the radio waves transmitted from the data-transfer radio-wave transmitter 25 to the corresponding data-transfer radio-wave receiver 30 such that the radio waves are exchanged only between the data-transfer radio-wave transmitter 25 and the data-transfer radio-wave receiver 30 in a corresponding relationship. The data-transfer radio-wave receiver 30 generates digital signals based on the radio waves transmitted from the data-transfer radio-wave transmitter 25 and guided by the shield 26. The data-transfer radio-wave receiver 30 transmits the digital signals to the data transmitter 10. The data transmitter 10 transmits the digital signals received from the data-transfer radio-wave receiver 30 to the data receiver 11 using a communication means such as, for example, optical communication.

According to an instruction from the frame control transmitter 3, the data receiver 11 transmits the digital signals received from the data transmitter 10 to the image reconstruction unit 12 in the console 1b. Upon a lapse of irradiation time of X-rays based on the settings entered in step S2 from the start of X-ray irradiation, the process proceeds to step S5.

In step S5, the system controller 2 notifies the frame control transmitter 3 of a control content for stopping the irradiation of X-rays. The frame control transmitter 3 transmits the notification from the system controller 2 to the X-ray irradiator 4. According to the control content received from the frame control transmitter 3, the X-ray irradiator 4 stops irradiating X-rays. Having stopped the irradiation of X-rays, the system controller 2 notifies the frame control transmitter 3 of a control content for stopping the rotation of the rotating part 1c. The frame control transmitter 3 transmits the notification from the system controller 2 to the rotating-part drive mechanism 17. The rotating-part drive mechanism 17 operates according to the control content received from the frame control transmitter 3 and stops the rotation of the rotating part 1c. Meanwhile, according to an instruction from the system controller 2, the image reconstruction unit 12 generates image data based on the digital signals received from the data receiver 11 and transmits the image data to the image storage 13. The image storage 13 stores the image data received from the image reconstruction unit 12. The system controller 2 displays an image on the display 14 based on the image data stored in the image storage 13. According to an instruction from the system controller 2, the display 14 displays the image based on the image data stored in the image storage 13.

In step S6, the operator refers to the image displayed on the display 14. Having finished referring to the image, the operator ends the operation of the X-ray CT apparatus 1.

As described above, according to the embodiment, the X-ray CT apparatus 1 wirelessly transmits signals inside the X-ray detector 5.

Figure 6A:
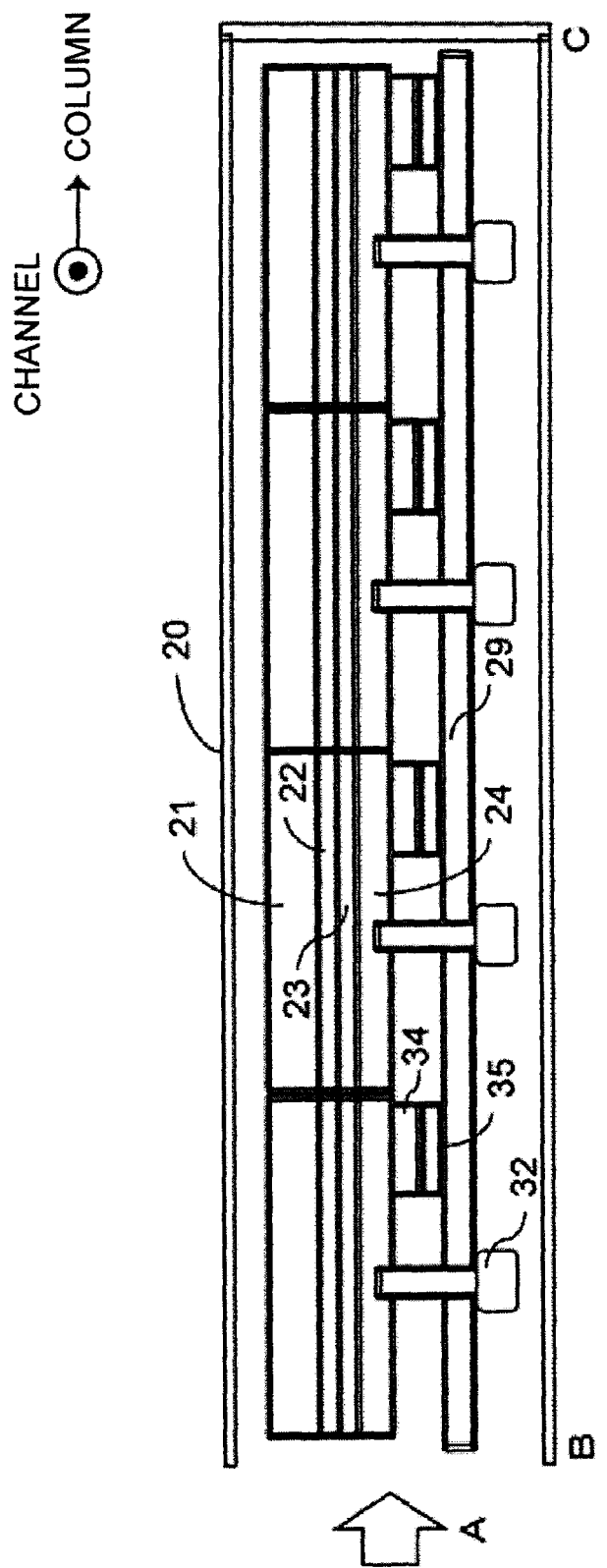
FIG. 6A is a schematic diagram illustrating the internal structure of an X-ray detector according to a first comparative example of the embodiment.

FIG. 6A is a schematic diagram illustrating an X-ray detector, which transmits signals by only wired communication, in a first comparative example of this embodiment.

In the X-ray detector of the first comparative example as illustrated in FIG. 6A, for example, a connector top 34 is fixed to the substrate 24, and a connector bottom 35 is fixed to the backplane 29. The connector top 34 is connected to the connector bottom 35 only when the position of the positioning pin 32 matches the position of the recess in the substrate 24. When the connector top 34 and the connector bottom 35 are connected to each other, a digital signal from the DAS chip 23 is transmitted via the connector top 34 and the connector bottom 35 to the data transmitter. In this type of X-ray detector, the connector top 34 and the connector bottom 35 include a plurality of pins for signal transmission, the number of which corresponds to the number of elements of one module, for example. Accordingly, if the position of the positioning pin 32 is deviated even slightly during, for example, the manufacture or maintenance, the connector top 34 cannot be connected to the connector bottom 35, thereby possibly causing a defect in the product. On the other hand, in the X-ray CT apparatus 1 of this embodiment, signals are transmitted wirelessly in this portion. Thus, even if the position of the positioning pin 32 is deviated to some extent, product defects are less likely to occur.

Figure 6B:
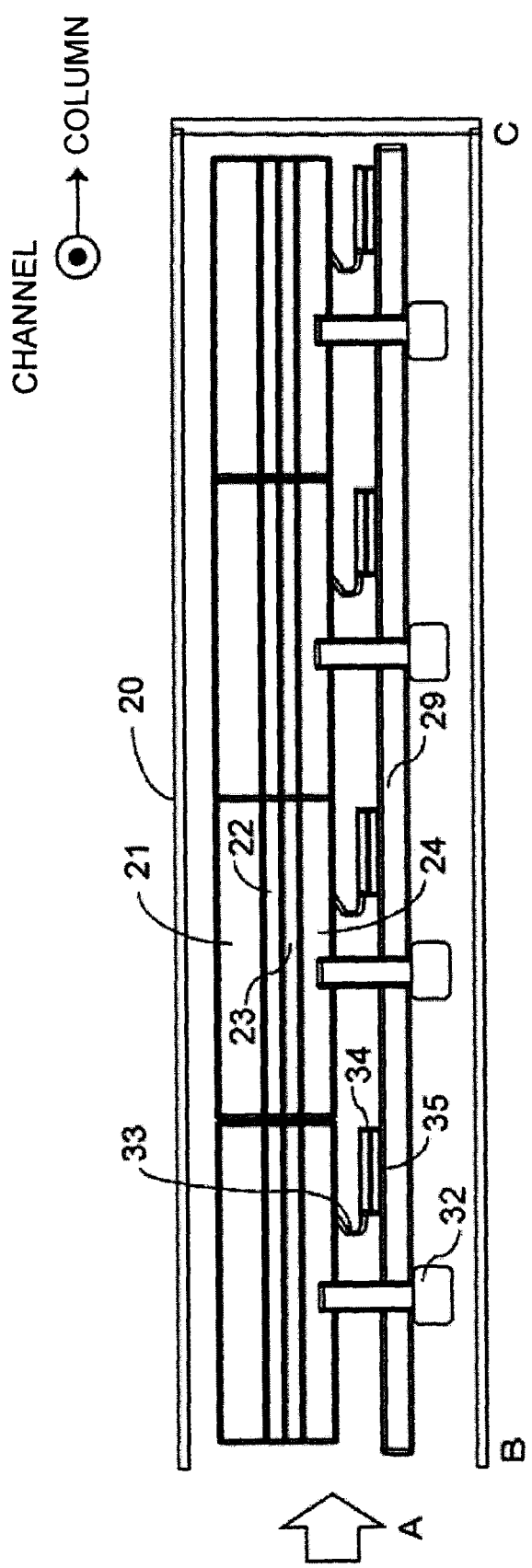
FIG. 6B is a schematic diagram illustrating the internal structure of an X-ray detector according to a second comparative example of the embodiment.

FIG. 6B is a schematic diagram illustrating another X-ray detector, which transmits data by only wired communication, in a second comparative example of this embodiment. In the X-ray detector of the second comparative example as illustrated in FIG. 6B, for example, one end of FPC 33 is fixed to the substrate 24, and the other end of the FPC 33 is fixed to the connector top 34. Besides, the connector bottom 35 is fixed to the backplane 29. When the connector top 34 and the connector bottom 35 are connected to each other, a digital signal from the DAS chip 23 is transmitted via the FPC 33, the connector top 34 and the connector bottom 35 to the data transmitter. In this type of X-ray detector, the connector top 34 and the connector bottom 35 located on the opening side B of the housing 20 are easy to be connected together in, for example, the manufacture or maintenance. However, the connector top 34 and the connector bottom 35 located on the inner side C of the housing 20 are difficult to be connected together. On the other hand, in the X-ray CT apparatus 1 of this embodiment, signals are transmitted wirelessly in this portion. Thus, even if the position of the positioning pin 32 is deviated to some extent, the signal transmission can be carried out, and product defects are less likely to occur. In addition, these parts do not need to be physically connected, which facilitates the installation of the X-ray detector 5 in the housing 20.

Further, noise due to the vibration of the FPC and the connector can be reduced while the X-ray CT apparatus is in operation.

Still further, it is possible to greatly improve the workability in mounting the modules 41 on the backplane 29 during the manufacture or maintenance of the X-ray detector 5.

In this embodiment, an example is described in which all the data-transfer radio-wave transmitters 25 transmit and receive radio waves of the same frequency. However, for example, adjacent pairs of the data-transfer radio-wave transmitters 25 may transmit signals of different frequencies such that each of the data-transfer radio-wave receivers 30 can be set to receive only signals of a frequency, at which corresponding one of the data-transfer radio-wave transmitters 25 transmits signals. That is, among a plurality of modules, a wireless communication unit of a first module wirelessly transmits and receives signals at a first frequency. Besides, a wireless communication unit of a second module, which is adjacent to the first module in the body axis direction of the subject, wirelessly transmits and receives signals at a second frequency that is different from the first frequency. In this case, signals can be prevented from being wrongly transmitted and received between the data-transfer radio-wave transmitter 25 and the data-transfer radio-wave receiver 30 not in a corresponding relationship.

In this embodiment, an example is described in which all the data-transfer radio-wave transmitters 25 transmit and receive radio waves at the same timing. However, for example, adjacent pairs of the data-transfer radio-wave transmitters 25 may transmit signals at different timings such that each of the data-transfer radio-wave receivers 30 can be set to receive signals only at a timing, at which corresponding one of the data-transfer radio-wave transmitters 25 transmits signals. That is, among a plurality of modules, a wireless communication unit of a first module wirelessly transmits and receives signals at a first timing. Besides, a wireless communication unit of a second module, which is adjacent to the first module in the body axis direction of the subject, wirelessly transmits and receives signals at a second timing that is different from the first timing. In this case, signals can be prevented from being wrongly transmitted and received between the data-transfer radio-wave transmitter 25 and the data-transfer radio-wave receiver 30 not in a corresponding relationship.

In this embodiment, an example is described in which the data-transfer radio-wave transmitter 25 transmits and receives radio waves in all the modules. However, at least one of the modules may include a wired communication unit (wired communication circuit) that transmits and receives signals via wire in at least a part between the detector 6 and the A/D converter 8 or between the A/D converter 8 and the data transmitter 10. That is, a first module of the plurality of modules that are divided in the Z-axis direction wirelessly transmits and receives signals through the wireless communication unit. Besides, a second module, which is different from the first module, transmits and receives signals via wire through the wired communication unit. The second module is located at the end of the modules. For example, as in the opening side B, the connectors can be easily connected to each other at the end. On the other hand, as in the inner side C, it is difficult to connect the connectors of the modules near the center at a distance from the end. Therefore, if signals are transmitted and received wirelessly in the part where connectors are difficult to be connected, a manufacturing defect is less likely to occur.

In this embodiment, an example is described in which digital signals are converted into radio waves, and transmitted and received wirelessly in a part between the A/D converter 8 and the data transmitter 10. Signals may be converted into radio waves, and transmitted and received wirelessly in at least a part between the detector 6 and the A/D converter 8 (e.g., between the detector 6 and the signal amplifier 7 or between the signal amplifier 7 and the A/D converter 8), between the detector 6 and the A/D converter 8, between the A/D converter 8 and the transmission controller 9, or between the transmission controller 9 and the data transmitter 10.

In this embodiment, an example is described in which signals are transmitted and received by using radio waves through a wireless communication unit. However, the wireless communication unit may transmit and receive signals by optical communication using light.

In this embodiment, an example is described in which electric power is supplied wirelessly in a part between the A/D converter 8 and the data transmitter 10. Electric power may be supplied wirelessly in a part between the detector 6 and the A/D converter 8 (e.g., between the detector 6 and the signal amplifier 7 or between the signal amplifier 7 and the A/D converter 8). In addition, while an example is described in which a current is converted into a radio wave, and electric power is supplied based on the transmission and reception of the radio wave, it is not so limited, and the use of non-contact power transmission may suffice. In this case, for example, electric power may be supplied using electromagnetic induction between coils arranged at positions corresponding to the power-supply radio-wave transmitter 31 and the power-supply radio-wave receiver 27. Alternatively, electric power may be supplied by using so-called electromagnetic resonance method that utilizes the resonance of an electromagnetic field.

In this embodiment, in the X-ray detector 5, at least an array of four modules arranged in the column direction may be installed as one unit. However, the modules may be installed separately. Besides, the number of modules in one unit can be arbitrarily determined, and, for example, two modules may be set as one unit.

In this embodiment, an example is described in which, in the X-ray detector 5, each module is provided with the positioning pin 32. However, the positioning pin 32 need not necessarily be provided to all the modules. For example, when one unit is made up of four modules, only two modules at both ends may be provided with the positioning pin 32, and remaining two may be provided with no positioning pin.

In this embodiment, an example is described in which the X-ray detector 5 includes modules which are divided in the column and channel directions. The X-ray detector 5 may include a plurality of modules which are divided in only the channel direction. In addition, a plurality of modules may constitute only the center part of the X-ray detector 5 but the edges in the column and channel directions. Although the X-ray detector of the embodiment is described as being applied to the X-ray CT apparatus, it may also be applicable to other medical imaging apparatuses. For example, the X-ray detector of the embodiment may be applied to a medical imaging apparatus that uses a variety of X-ray detectors such as an X-ray imaging apparatus provided with an X-ray tube at one end of the C-shaped arm and an X-ray detector at the other end.

While certain embodiments have been described, these embodiments have been presented by way of example only, and are not intended to limit the scope of the inventions. Indeed, the novel embodiments described herein may be embodied in a variety of other forms; Further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray detector comprising:
   a detector configured to detect X-rays emitted from an irradiator and generate an analog signal;
   an analog-to-digital converter configured to convert the analog signal to a digital signal; and
   a data transmitter configured to receive the digital signal from the analog-to-digital converter, wherein
   signals are wirelessly transmitted and received in at least a part between the detector and the analog-to-digital converter or between the analog-to-digital converter and the data transmitter.

2. An X-ray CT apparatus comprising:
   a fixed part;
   a rotating part configured to be rotatably attached to the fixed part to rotate around a subject;
   an irradiator arranged in the rotating part;
   a detector arranged in the rotating part, and configured to detect X-rays emitted from the irradiator and generate an analog signal;
   an analog-to-digital converter arranged in the rotating part, and configured to convert the analog signal to a digital signal;
   a data transmitter arranged in the rotating part, and configured to receive the digital signal from the analog-to-digital converter; and
   a data receiver arranged in the fixed part, and configured to receive the digital signal transmitted from the data transmitter, wherein
   signals are wirelessly transmitted and received in at least a part between the detector and the analog-to-digital converter or between the analog-to-digital converter and the data transmitter.

3. The X-ray CT apparatus of claim 2, wherein the rotating part further includes:
   a receiver;
   a support member supporting the receiver, the receiver receiving radio waves into which the digital signal from the analog-to-digital converter is converted and generating the digital signal based on the radio waves; and a substrate on which the detector and the analog-to-digital converter are arranged, the substrate configured to be removably attached to the support member.

4. The X-ray CT apparatus of claim 3, wherein
the digital signal is wirelessly transmitted and received in at least a part between the analog-to-digital converter and the data transmitter, and the receiver is configured to transmit the digital signal to the data transmitter, one of the support member and the substrate includes a positioning pin, another of the support member and the substrate has a recess, into which the positioning pin is insertable, and the support member and the substrate are engaged with each other by insertion of the positioning pin in the recess.

5. The X-ray CT apparatus of claim 2, further comprising a wireless power supply configured to supply electric power wirelessly in at least a part between the detector and the analog-to-digital converter or between the analog-to-digital converter and the data transmitter.

6. An X-ray CT apparatus comprising:
a fixed part; and
a rotating part configured to be rotatably attached to the fixed part to rotate around a subject; wherein
the fixed part includes a data receiver,
the rotating part includes an irradiator, an X-ray detector, and a data transmitter,
the X-ray detector including:
  a detector configured to detect X-rays emitted from the irradiator, and generate an analog signal,
  an analog-to-digital converter configured to convert the analog signal to a digital signal,
  a data-transfer radio-wave transmitter, and
  a data-transfer radio-wave receiver, the data-transfer radio-wave transmitter receives the digital signal transmitted from the analog-to-digital converter, converts the digital signal received into radio waves of a predetermined frequency, and wirelessly transmits the radio waves to the data-transfer radio-wave receiver, the data-transfer radio-wave receiver receives the radio waves transmitted from the data-transfer radio-wave transmitter, generates digital signal based on the radio waves received, and transmits the digital signal generated to the data transmitter, and the data transmitter receives the digital signal transmitted from the data-transfer radio-wave receiver, and transmits the digital signal received to the data receiver.

7. The X-ray CT apparatus of claim 6, wherein
the X-ray detector includes modules which are arrayed in at least a body axis direction of the subject,
the radio waves are transmitted and received in each of the modules,
the modules include a first module and a second module,
in the first module, the radio waves are transmitted and received at a first timing, and
in the second module, radio waves are transmitted and received at a second timing that is different from the first timing.

8. The X-ray CT apparatus of claim 6, wherein,
the X-ray detector includes modules which are arrayed in at least a body axis direction of the subject,
the radio waves are transmitted and received in each of the modules,
the modules include a first module and a second module,
in the first module, radio waves are transmitted and received at a first frequency, and
in the second module, radio waves are transmitted and received at a second frequency that is different from the first frequency.

* * * * *